United States Patent
Jackels et al.

(10) Patent No.: US 8,568,566 B2
(45) Date of Patent: Oct. 29, 2013

(54) METHOD AND APPARATUS FOR MAKING ABSORBENT STRUCTURES WITH ABSORBENT MATERIAL

(75) Inventors: Hans Adolf Jackels, Euskircken (DE); Carsten Heinrich Kreuzer, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/491,936

(22) Filed: Jun. 8, 2012

(65) Prior Publication Data

US 2012/0312491 A1 Dec. 13, 2012

(30) Foreign Application Priority Data

Jun. 10, 2011 (EP) .................................... 11169396

(51) Int. Cl.
*D21F 1/48* (2006.01)
(52) U.S. Cl.
USPC ........... 162/297; 162/116; 162/289; 162/318; 118/239; 118/244; 156/276; 156/305
(58) Field of Classification Search
None
See application file for complete search history.

(56) References Cited

U.S. PATENT DOCUMENTS

| | | | |
|---|---|---|---|
| 4,940,464 A | 7/1990 | Van Gompel et al. | |
| 5,092,861 A | 3/1992 | Nomura et al. | |
| 5,246,433 A | 9/1993 | Hasse et al. | |
| 5,562,646 A | 10/1996 | Goldman et al. | |
| 5,569,234 A | 10/1996 | Buell et al. | |
| 5,607,760 A | 3/1997 | Roe et al. | |
| 5,609,587 A | 3/1997 | Roe | |
| 5,635,191 A | 6/1997 | Roe et al. | |
| 5,643,588 A | 7/1997 | Roe et al. | |
| 5,897,545 A | 4/1999 | Kline et al. | |
| 5,957,908 A | 9/1999 | Kline et al. | |
| 6,120,487 A | 9/2000 | Ashton | |
| 6,120,489 A | 9/2000 | Johnson et al. | |
| 6,585,858 B1 * | 7/2003 | Otto et al. | 162/161 |
| 2001/0016548 A1 | 8/2001 | Kugler et al. | |
| 2002/0056516 A1 | 5/2002 | Ochi | |
| 2003/0084983 A1 * | 5/2003 | Rangachari et al. | 156/181 |
| 2003/0233082 A1 | 12/2003 | Kline et al. | |
| 2006/0069371 A1 | 3/2006 | Ohashi et al. | |
| 2007/0246147 A1 | 10/2007 | Venturino et al. | |
| 2008/0274227 A1 * | 11/2008 | Boatman et al. | 425/403 |
| 2010/0051166 A1 | 3/2010 | Hundorf et al. | |
| 2011/0130732 A1 * | 6/2011 | Jackels et al. | 604/365 |

FOREIGN PATENT DOCUMENTS

| | | |
|---|---|---|
| EP | 0 691 133 A1 | 1/1996 |
| EP | 1 621 166 A1 | 2/2006 |
| WO | WO 2009/152018 A1 | 12/2009 |

OTHER PUBLICATIONS

European Search Report, EP11169396.6, dated Oct. 21, 2011, 9 pages.
International Search Report, PCT/US2012/041522, dated Sep. 5, 2012, 13 pages.

* cited by examiner

*Primary Examiner* — Richard Crispino
*Assistant Examiner* — Eric Yaary
(74) *Attorney, Agent, or Firm* — Charles R. Matson; Andrew A. Paul; Richard Alexander

(57) ABSTRACT

Apparatus and method for producing absorbent structures with absorbent layers with channel(s) without absorbent material, using a first moving endless surface with specific raised strip(s) and a second moving endless surface with specific mating strip(s).

12 Claims, 5 Drawing Sheets

METHOD AND APPARATUS FOR MAKING ABSORBENT STRUCTURES WITH ABSORBENT MATERIAL

CROSS REFERENCE TO RELATED APPLICATION

This application claims priority to European Patent Convention Application 11169396.6, filed Jun. 10, 2011, the substance of which is incorporated herein by reference.

FIELD OF THE INVENTION

The present disclosure relates to a method for making an absorbent structure with strips that are free of absorbent material, by receiving absorbent material on a first surface with raised strips that do not receive absorbent material, and transferring it therewith to a second surface with mating strips, that meet with said raised strips, and that then do not receive absorbent material; and to apparatuses combining such first and second surfaces.

BACKGROUND OF THE INVENTION

Absorbent articles, such as diapers and sanitary napkins, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine-loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Efforts have also been made to make absorbent article thinner when dry, to improve the comfort of such articles.

Some absorbent articles, like diapers, contain absorbent material such as super absorbent polymers that absorbs very high quantities of liquid and causes the absorbent article to swell significantly. Such articles will thus increase significantly in volume during use, and sometimes in particular in the crotch area between the wearer's legs, which may render the article uncomfortable.

There is thus still a need to further improve the fit of such articles and/or the liquid transportation away from the crotch. There is also a need to reduce the usage of absorbent material in such articles.

There is also still a need to further reduce the chance of leakage and to improve the efficiency of absorbency of an absorbent article, such as a diaper.

It has also been found that improved liquid transportation can be achieved by the provision of transportation channels for distributing liquid in the absorbent article, e.g. the absorbent structure thereof. Furthermore, it has surprisingly been found that the amount of absorbent material can be reduced hereby, whilst maintaining the performance. It has been found that improved fit can be obtained by providing absorbent articles with absorbent structures wherein the absorbent material is structured in machine direction, optionally with areas that comprise less or no absorbent material, for improved bending flexibility in use (in the direction corresponding to the machine direction).

The present disclosure provides an apparatus and method for providing such absorbent structures, having suitable transportation channels, which allow reduction of the usage of absorbent material and/or channels that improve fit/flexibility.

SUMMARY OF THE INVENTION

The present disclosure provides an apparatus (1) for making an absorbent structure comprising a supporting sheet (200) and thereon an absorbent layer with a longitudinal dimensional and transverse dimension and a height dimension, said absorbent layer comprising an absorbent material (100) with therein one or more channels that are substantially free of absorbent material, said apparatus (1) having:
  a) a feeder (60) for feeding said absorbent material (100) to a first moving endless surface;
  b) a transfer means for transferring a supporting sheet (200) to a second moving endless surface;
  c) a first moving endless surface (20), having one or more absorbent layer-forming reservoirs (25) with a longitudinal dimension and averaged length, a perpendicular transverse dimension and average width, and, perpendicular to both, a depth dimension and average depth, and a void volume for receiving said absorbent material (100) therein, said reservoir(s) comprising one or more substantially longitudinally extending raised strips (21) (not having a void volume and hence not receiving said absorbent material (100) therein), each having an average width W of at least 5% of the average width of the reservoir (25) (in some embodiments optionally at least 5 mm), and an average length L of at least 5% and at the most 80% of the average longitudinal dimension of the reservoir; said reservoir(s) being for transferring said absorbent material (100) to said second moving endless surface (30) adjacent and in proximity thereto;
  d) said second moving endless surface (30), having an outer shell that has one or more air permeable or partially air permeable receptacles (33) for receiving said supporting sheet (200) thereon or therein, and said receptacle (33) having one or more substantially longitudinally extending substantially mating strips (31), having each an average width W' of from 0.5×W to 1.2×W, optionally at least 2.5 mm, optionally having an average length L' being from about 0.8×L to 1.2×L provided at the most 90% of the longitudinal dimension of the reservoir,
wherein said outer shell is optionally connected to one or more secondary vacuum systems for facilitating retention of said supporting sheet (200) and/or said absorbent material (100) thereon, and
wherein, in a meeting point, said first moving endless surface (20) and said outer shell and/or second moving endless surface (30) are adjacent to one another and in close proximity of one another during transfer of said absorbent material (100) and wherein each mating strip (31) is adjacent and in close proximity to a raised strip (21) during transfer of said absorbent material.

The invention also provides methods using said apparatus (1) of the invention, and/or for making an absorbent structure with a longitudinal dimensional and transverse dimension and height dimension, and comprising a supporting sheet (200) and thereon an absorbent layer of absorbent material (100) and therein one or more channels with substantially no absorbent material, said method comprising the steps of:
  a) providing a feeder (60) for feeding said absorbent material (100) to a first moving endless surface;
  b) providing a transfer means for transferring a supporting sheet (200) to a second moving endless surface;

c) providing a first moving endless surface (20), having one or more absorbent layer-forming reservoirs (25) with a longitudinal dimension and averaged length, a perpendicular transverse dimension and average width, and, perpendicular to both, a depth dimension and average depth, and a void volume for receiving said absorbent material (100) therein, said reservoir(s) comprising one or more substantially longitudinally extending raised strips (21), each having an average width W of at least 5% of the average width of the reservoir, and an average length L of at least 5% and at the most 80% of the average longitudinal dimension of the reservoir; said reservoir(s) being for transferring said absorbent material (100) to said second moving endless surface (30) adjacent and in proximity thereto;

d) providing a second moving endless surface (30), having an outer shell that has one or more air permeable or partially air permeable receptacles (33) with for receiving said supporting sheet (200) thereon or therein, with a receiving area and with one or more substantially longitudinally extending mating strips (31) that may be air impermeable, and having each an average width W' of from 0.5×W to 1.2×W, an average length L' being from about 0.8×L to 1.2×L provided at the most 90% of the longitudinal dimension of the reservoir, wherein said outer shell is optionally connected to one or more secondary vacuum systems for facilitating retention of supporting sheet (200) and/or said absorbent material (100) thereon, and wherein, in a meeting point, said first moving endless surface (20) and said second surface (30) outer shell are at least partially adjacent to one another and in close proximity of one another during transfer of said absorbent material (100) and such that each mating strip (31) is substantially completely adjacent and in close proximity to a raised strip (21) during transfer of said absorbent material;

e) feeding with said feeder (60) an absorbent material (100) to said first moving endless surface, in at least said reservoir(s) (25) thereof;

f) optionally, removing any absorbent material (100) on said raised strips (21);

g) simultaneously, transferring said supporting sheet (200) to said second moving endless surface, onto or into said receptacle (33);

h) selectively transferring in said meeting point, said absorbent material (100) with said first moving endless surface (20) only to said part of the supporting sheet (200) that is on or in said receiving area of said receptacle (33).

Said reservoir(s) (25) may be formed by of a multitude of grooves and/or cavities (22) with a void volume, for receiving said absorbent material (100) therein. In some embodiments, the average width W of (each) strip is optionally at least 6 mm, or for example at least 7 mm, and/or at least at least 7%, or for example at least 10% of the average width of the respective reservoir.

Said grooves and/or cavities (22) may each for example have a maximum dimension in transverse direction which is at least 3 mm, and wherein the shortest distance between directly neighboring cavities (22) and/or grooves in substantially transverse dimension, is less than 5 mm. Cavities (22) and/or grooves that are directly adjacent a raised strip (21) may have a volume that is more than the volume of one or more, or all of their neighboring cavities (22) or grooves, that are not directly adjacent said strip or another strip (thus further removed from a strip).

Said first moving endless surface's reservoir (25) may be at least partially air permeable and said first moving endless surface (20) may have a cylindrical surface with said reservoirs, rotatably moving around a stator, comprising a vacuum chamber (28) (and optionally a blow of chamber (29) to blow pressurized air through the reservoir onto said absorbent material just before the meeting point); said second moving surface's outershell may be cylindrical, rotatably moving around a stator, comprising a secondary vacuum chamber (38) connected to said secondary vacuum system (and optionally a blow of chamber (39) to blow pressurized air through the receptacle onto said absorbent structure to facilitate removal from the second moving endless surface).

Said receptacle(s) (33) may further comprise a multitude of substantially longitudinally extending rods (36), spaced apart from one another in transverse direction, for example, each rod having a maximum cross-machine dimension of at least 0.3 mm and the minimum distance in transverse dimension between neighboring rods (36) being at least 1 mm, and said rods (36) each having an average height dimension of at least 1 mm, optionally said rods (36) and said mating strips (31) being in the same plane of the outershell.

The apparatus (1) may comprise one or more adhesive application unit(s) (50;51) as described herein. Said adhesive application can be beneficial to immobilize said absorbent material, to ensure said channels remain substantially permanent in use and/or to help the supporting material adhere to a further material placed over said absorbent layer in said channels. The method may comprise the addition a step i):

i) 1) applying an adhesive material (i.e. a first adhesive material) to said absorbent structure produced in step g); and/or i) 2) applying an adhesive material (i.e. a second adhesive material) to said supporting sheet (200), prior or step f, or simultaneously therewith, but in any event prior to step h).

Step i) 1) may involve straying said first adhesive material in the form of fibers onto said absorbent layer, or part thereof, for example substantially continuously, so it is also present in said channels.

Step i) 2) may involve slot coating or spray-coating the supporting sheet (200), either continuously, or for example in a pattern corresponding to the channel pattern.

In some preferred embodiments herein, the apparatus (1) may have pressure roll (70) with a raised pressure pattern (71), substantially corresponding to the pattern of said mating strip(s) (31) and/or channels, for contacting selectively said absorbent structure's supporting sheet (200) and/or the further material, described herein after, in the areas corresponding to said channel (s) (only).

Said receptacle (33) of said second moving surface may have a first average width dimension and said supporting sheet (200), or said part thereof that is on said receptacle (33), has a second average width dimension, and the ratio of said first to said second average width dimension is at least 1:1.2.

By use of method and apparatus (1) herein, wherein the raised portions and mating strips (31) substantially mate during transfer of the absorbent material (100) to a supporting sheet (200) on said receptacle (33), e.g. on said mating strips (31), the absorbent structure may have said absorbent material (100) deposited on a layer with therein channels substantially without absorbent material; the absorbent layer may be in the form of strips of absorbent material (100) with therein, or therein between strips free of absorbent material (e.g. the crests of said supporting sheet (200)); in some embodiments herein, the supporting sheet (200) is formed into undulation (s) between neighboring matting strips, and/or between neighboring rods (36) that may be present, as described below, and the method and apparatus (1) herein is such that the absorbent material (100) is deposited in said undulations.

As described above, the supporting sheet (200) may be transferred to said second moving endless surface (30) such that it forms undulations and crests. Then, when the supporting sheet (200) is removed from said second moving endless surface, the supporting sheet (200) is pulled substantially flat, resulting in an absorbent structure with substantially longitudinally extending strips (that correspond to the crests of said material) that comprise substantially no absorbent material.

The invention also relates to absorbent structures, cores obtainable by the method herein or with the apparatus herein, and absorbent articles, such as pads or in particular diapers, comprising such a structure or core.

It should be understood that above and following description applies equally to the method and the apparatus (1) of the invention, and the absorbent structure obtained therewith, unless stated otherwise.

DETAILED DESCRIPTION OF THE INVENTION

Figure 1A:
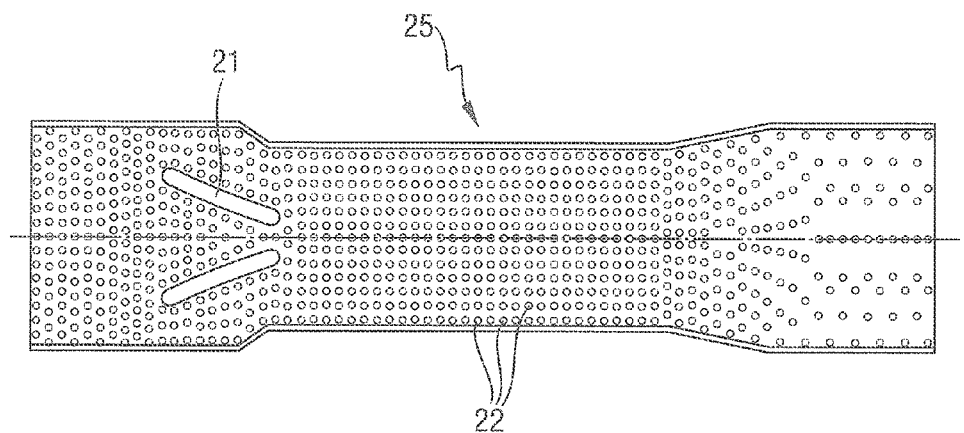
FIG. 1A is a top view of a reservoir (25) of the first moving endless surface (20) herein.

As summarized above, this invention encompasses a method and apparatus (1) for making an absorbent structure useful for absorbent article comprising absorbent material, optionally at least, or only, particulate superabsorbent polymer material, and preferred absorbent structure. Embodiments of such method and apparatus (1) and resulting absorbent structures and absorbent articles are further described herein after the following definitions.

Definitions

"Absorbent structure" refers to a three-dimension structure with a longitudinally dimension and perpendicular thereto a transverse dimension and perpendicular to both a height dimension, and that comprises at least an absorbent material (100) and a supporting sheet (200), and that is useful in an absorbent article.

"Absorbent layer" refers to a three dimensional layer of absorbent material, formed by deposition of absorbent material (100) onto the supporting sheet (200).

"Absorbent material" refers to a material or mixture of materials that can absorb and retain bodily fluids; it typically includes or consists of "superabsorbent polymer material". "Superabsorbent polymer material" (also known as "absorbent gelling material," or "AGM," or "superabsorbent,") refer to polymeric material that can absorb at least 10 times 9 and typically t least 15 times or at least 20 times) their weight of an aqueous 0.9% saline solution as measured using the Centrifuge Retention Capacity test (Edana 441.2-02), i.e. having a CRC of at least 10 g/g, and typically at least 15 g/g or at least 20 g/g.

"Particulate" is used herein to refer to a material which is in particulate form so as to be flowable in the dry state.

"Absorbent article" refers to a device that absorbs and contains body exudates, and, more specifically, refers to devices that are placed against or in proximity to the body of the wearer to absorb and contain the various exudates discharged from the body. Absorbent articles may include adult and infant diapers, including pants, such as infant training pants and adult incontinence undergarments, and feminine hygiene products, such as sanitary napkins and panty-liners and adult in continent pads, and breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

"Diaper" refers to an absorbent article generally worn by infants and incontinent persons about the lower torso so as to encircle the waist and legs of the wearer and that is specifically adapted to receive and contain urinary and fecal waste.

"Pant" or "training pant", as used herein, refer to diaper having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Substantially cellulose free" is used herein to describe an article, such as an absorbent layer structure or core, that contains less than 5% by weight cellulosic fibers.

"Thickness" and "height" are used herein interchangeably.

A absorbent structure and absorbent layer thereof, and a receptacle (33) and a reservoir (25) herein each have a longitudinal dimension and average length, and this may be corresponding the machine direction (MD, and perpendicular thereto a transverse dimension, and average width, which may be corresponding to the cross-machine direction (CD); and a front region, back region and central region, each being ⅓ of the average length of the structure/layer, respectively, and having each the full width. Each has longitudinal edges and edge zones, extending the full length thereof—as further described below.

First Moving Endless Surface, e.g. Print Roll

The absorbent material (100) is delivered to the supporting sheet (200) by a first moving endless surface (20) placed adjacent and in close proximity to said second moving endless surface, for example substantially above said surface. The absorbent material (100) may be deposited substantially continuously. The point or area where the absorbent material (100) leaves the first moving endless surface (20) and transfers to said second moving endless surface (30) is herein referred to as meeting point; and in this point or area a raised strip (21), e.g. each raised strip, mates with a mating strip (31), e.g. without direct contact.

A feeder (60) may deliver the absorbent material (100) to said first moving endless surface. Such as feeder (60) is capable of containing the absorbent material (100) and letting it flow to the supporting sheet (200) on said second moving endless surface, for example continuously. The feeder (60) may be a (e.g. stationary) hopper with a container portion, to hold the material, e.g. having a volume of at least 1000 cm$^3$, and it may have a guiding portion, e.g. a pipe-shapes portion, that guides the material from the container portion to the first moving endless surface.

Figure 2:
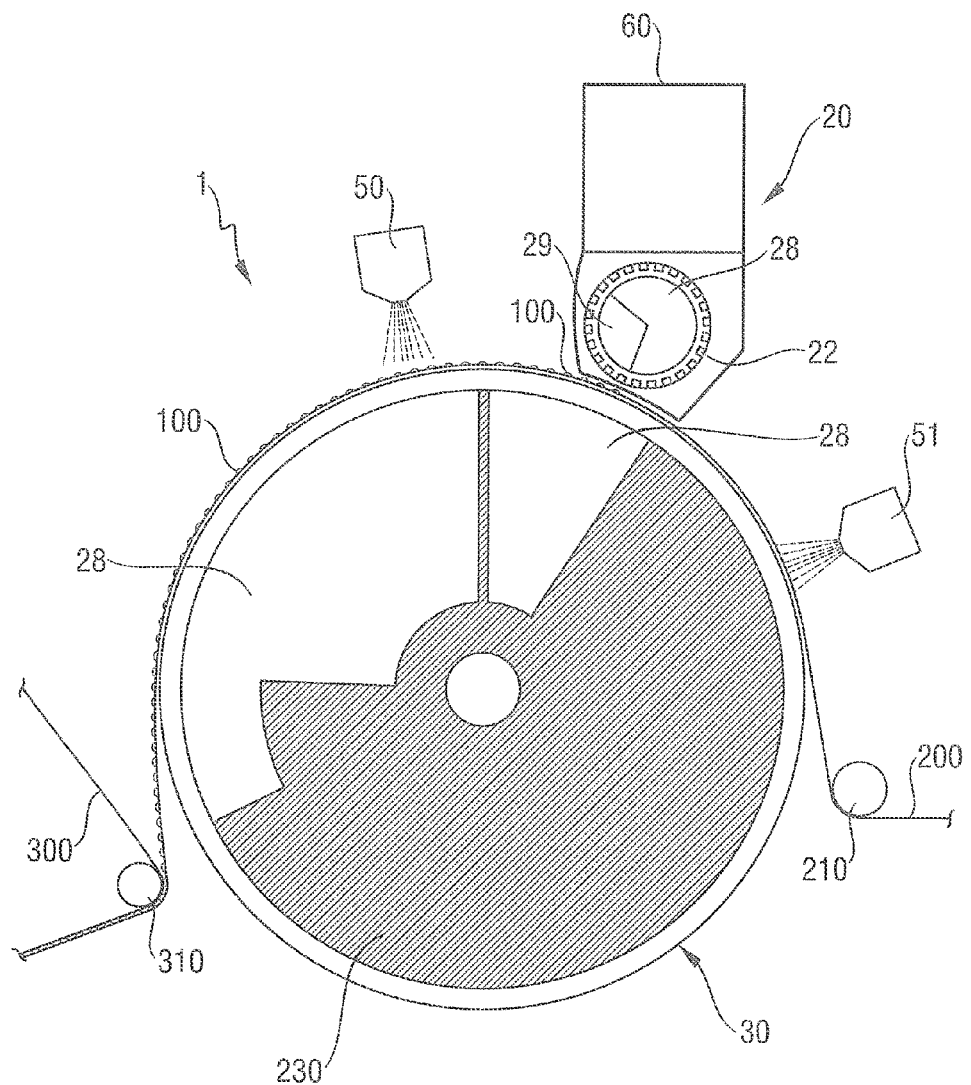
FIG. 2 is a side view of an apparatus (1) of the present disclosure, or used in the method of the invention.
Figure 3:
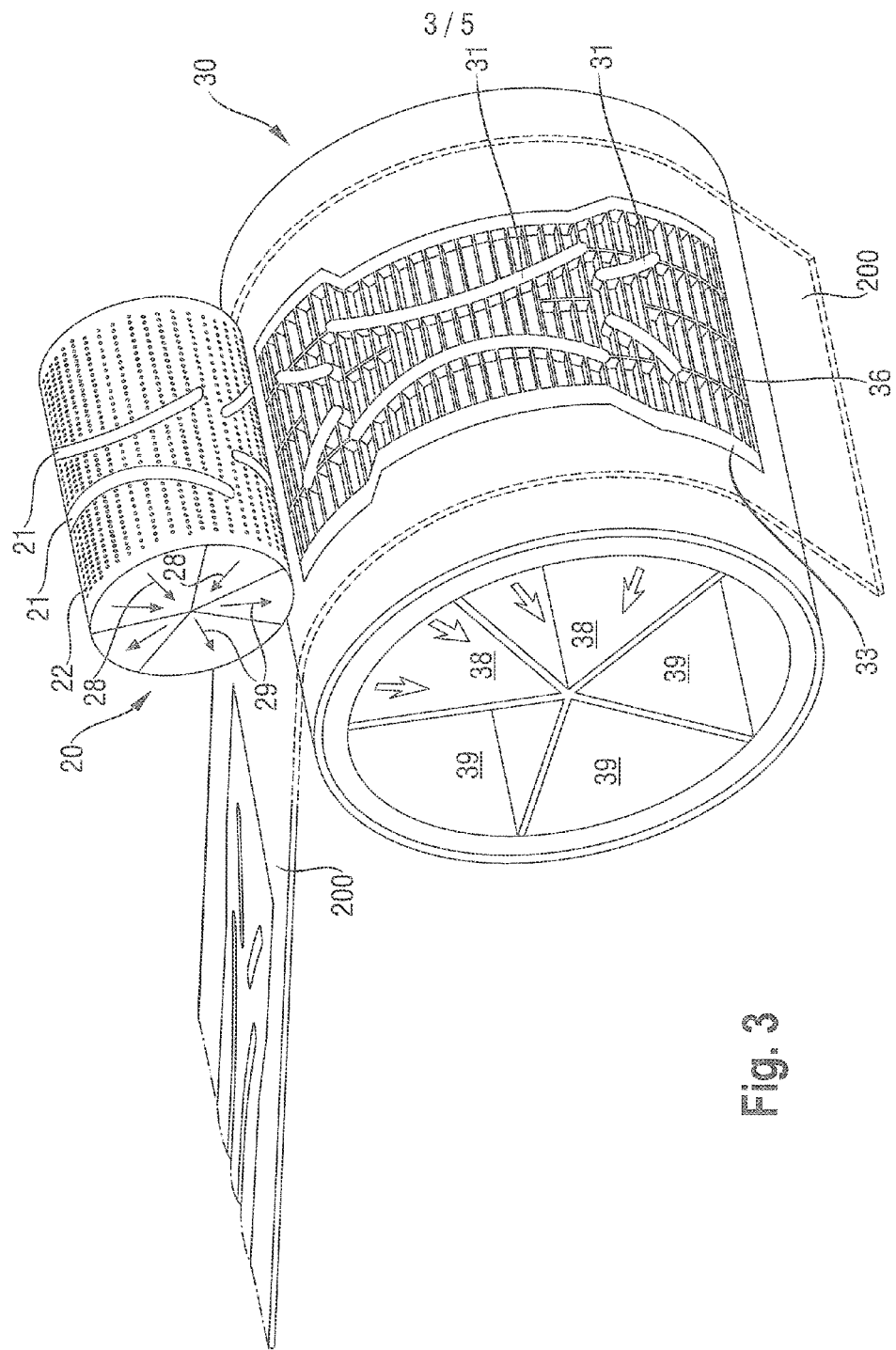
FIG. 3 is a partial perspective view of an apparatus (1) of the present disclosure, or used in a method of the invention.
Figure 4:
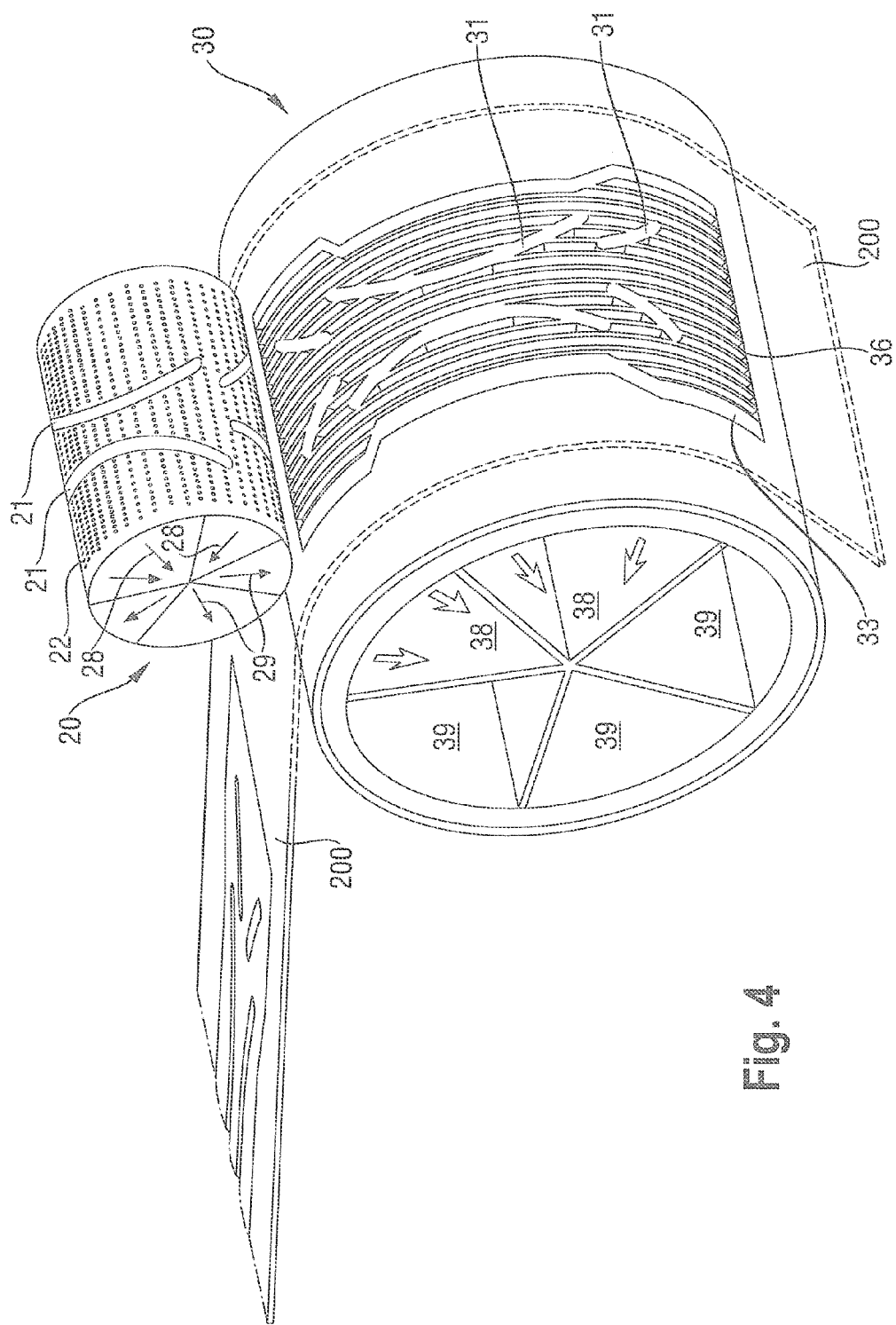
FIG. 4 is a partial perspective view of an alternative apparatus (1) of the present disclosure, or used in an alternative method of the invention.
Figure 5:
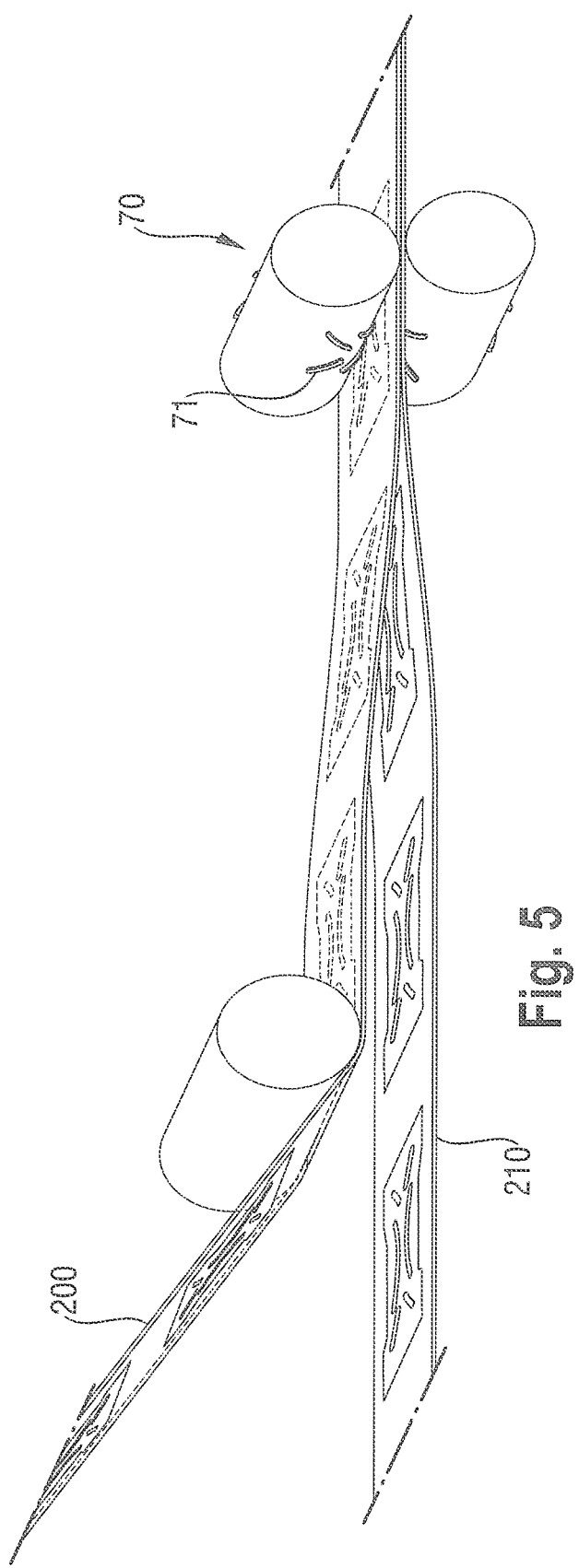
FIG. 5 is a partial perspective view of an optional element of apparatus (1) of the present disclosure, or optionally used in a method of the invention.

The first moving endless surface (20) may be a rotating roll or drum, as for example shown in the FIGS. 2, 3 and 4. The radius of the first moving endless surface (20) may depend on what absorbent structure is produced, e.g. what size, and for example how many structures are produced per cycle of the first moving endless surface, e.g. print roll or drum. For example, the drum/print roll may have a radius of at least 40 mm, or of at least 50 mm; it may be for example up to 300 mm, or up to 200 mm. In some embodiments, the radius of the first moving surface is less than 50% of the radius of the second moving endless surface.

The first moving endless surface (20) may have any suitable width, but for example a width (for example in CD, hence perpendicular to MD) corresponding (substantially) to the width of the absorbent structure to be produced; this for example be at least 40 mm, or at least 60 mm, or for example up to 400 mm, or up to 200 mm.

Said first moving endless surface (20) may have one or more reservoirs with a certain volume for receiving said absorbent material (100) therein, and transporting it to and then depositing it on said supporting sheet (200) on a second moving endless surface.

Each reservoir (25) corresponds typically to an absorbent structure to be produced, as suitable for an absorbent article. The supporting sheet (200) may be a web material, so the method and apparatus (1) herein can thus serve to produce a web of such absorbent structures that are then subsequently separated into individual structures.

The reservoir (25) is at least partially air-permeable. It typically has an area that serves to receive said absorbent material, and this area is substantially in air-communication with a vacuum system, i.e. air permeable.

Figure 1B:
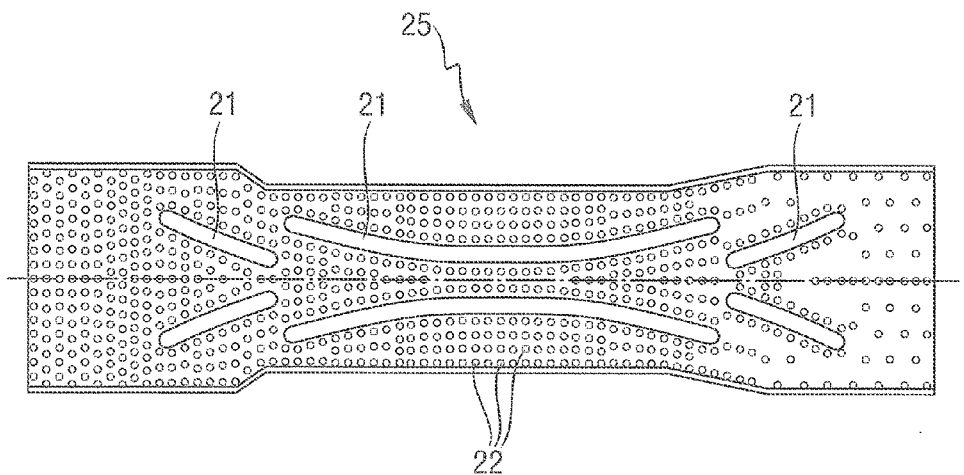
FIG. 1B is a top view of an alternative reservoir (25) of the first moving endless surface (20) herein.

As for example shown in FIGS. 1A and 1B and FIG. 3, the reservoir (25) has one or more raised strips (21) (that have no void volume) and that, when the first moving endless surface (20) moves (rotates) adjacent said second moving endless surface (30) with said supporting sheet (200) on said mating strips (31), said raised strips (21) mate substantially coincide (herein referred to as: mate) with said mating strips (31). Then, the absorbent material (100) is deposited selectively on the substrate material on the portions thereof that are not on said mating strips (31), to form an absorbent layer on a supporting sheet (200), having channels (strips) that are substantially free of absorbent material. A reservoir (25) has typically the same number of raised strips (21) as the number of mating strips (31) of the second moving endless surface.

Said strip(s) (21) may not be in air communication with a vacuum system that is in air communication with said first moving endless surface, i.e. the raised strips (21) may be air impermeable. They may have thereto have surfaces that have no apertures. The remaining area of the reservoir (25) that has void volume for receiving the absorbent material, thus excluding the raised strips (21), may be in air-communication with a vacuum system, e.g. having apertures in air-communication with a vacuum system.

The reservoir (25) has peripheral edges, and peripheral edge zones, including opposing longitudinal edges and edge zones, and a transverse front edge and front edge zone, and a transverse back edge and back edge zone. Each of said front and back edge zones, extending the complete transverse dimension, may for example have a longitudinal dimension of from about 5% to about 20%, or to 15%, or to 10% of the average longitudinal dimension of the reservoir. Each of said longitudinal edge zone may extend the length of the reservoir (25) and may have an average transverse dimension of for example from about 5% to about 20%, or typically to about 15% or to about 10% of the total average transverse dimension of the reservoir. In some embodiments herein, said raised strip(s) are not present in any of said edge zones.

The reservoir (25) may in addition, or alternatively, comprise a front region, back region and central region, therein between, as further described below. The central region may be for example the central ⅓ of the reservoir, extending the full transverse dimension. In some embodiment, the raised strips (21) are present only in the front region; alternatively, in some embodiments, the raised strips (21) are present in the central region only or at least; alternatively, in some embodiments, the raised strips (21) are present in the central region and front region and optionally in the back region. It may alternatively or in addition be preferred that one or more raised strips (21) are present in the central region and front region. To provide improved liquid transportation and more efficient absorbency by the whole absorbent structure, it may be preferred to have said raised strip(s) at least in the central region and optionally extending also at least in the front region.

In any such case, it may be preferred that none of the edge zones described above comprises such raised strips (21).

As for example shown in FIGS. 3 and 4, a raised strip (21) meets (and hence mates with) a mating strip (31) during the transfer of the absorbent material (100) herein, i.e. during absorbent material (100) transfer to said second moving endless surface, said raised strip (21) substantially overlaps said mating strip. This typically applies to each mating raised strip (21) and mating strip. In other words, each raised strip (21) typically has a corresponding mating strip. It should be understood that the raised strip (21) and mating strip (31) do not directly touch during the absorbent material (100) transfer (the supporting sheet (200) material is in between them). The supporting sheet (200) may or may not touch the raised strip(s).

The following is described for a raised strip, in relation to its corresponding mating strip, but may be, applicable to each raised strip.

A raised strip (21) and the corresponding mating strip (31) may have the same size and shaped and surface area, and be hence completely mating. It may be that a raised strip (21) has a surface area that is slightly more than the surface area of a corresponding mating strip. Hereby, the mating strip (31) and the corresponding raised strip (21) then typically still have substantially the same overall shape. Preferred length ratios and dimensions are herein described above and below.

In some embodiments, it may be preferred (in addition or as alternative of the above) that a mating strip (31) may have an average width W' that is less than the average width W of the raised strip, but in some embodiments, W' is not more than W, as further described above and below.

W is at typically least 5 mm, or for example at least 6 mm. or for example at least 7 mm or for example at least 8 mm, and for example less than 40 mm or less, or less 30 mm or less, or for example 20 mm or less.

A raised strip (21) extends typically at the most 80% or at the most 70% of the longitudinal dimension of the reservoir.

Thus, the average length of a raised strip (21) may be 80% or less of the average length of the reservoir, or for example at the most 70%.

The raised strips (21) are substantially longitudinally extending. They may be straight or for example curved, with a radius of curvature as describe herein, or angled, as described herein below.

The reservoir (25) may have for example at least two raised strips (21) on either side of the longitudinal axis of the reservoir, and being mirror images of one another. This is for example shown in FIG. 1A.

The reservoir (25) may also for example have 3 or 4, or for example 5 or for example 6 raised strips (21). Two or more thereof may be parallel to one another. The reservoir (25) may have for example 3, or 4, or 5, or 6 raised strips (21) that are at least present in the central region, and optionally extend in the front region and optionally in the back region; they may be parallel to one another and/or they may be such that those on one longitudinal side of the longitudinal axis of the reservoir (25) are mirror images of those that are on the opposite longitudinal side. This is for example shown in FIG. 1B.

The reservoir (25) may have for example two raised strips (21) in the front region, on either side of the longitudinal axis, and mirror images of one another therein; and two raised strips (21), extending in at least the central region, on either side of the longitudinal axis, and mirror images of one another therein; and optionally two raised strips (21) in the back region, on either side of the longitudinal axis, and mirror images of one another therein.

In some embodiments, there may be no raised strip (21) coinciding with the longitudinal axis of the reservoir, but only on either side thereof. This may help to ensure an absorbent structure formation into a U-shape during use, rather than a V-shape, which may be better for fit and/or absorbency.

In some embodiments, at least two raised strips (21) extend, and hence have an average length of, at least 50% of the average length of said reservoir. In some embodiments, there are at least an additional two raised strips (21) that have an average length that is less than 50% of the average length of the reservoir.

The raised strip's cross-section in the X-Z plane (X being transverse dimension; Z being height dimension) may be any form. It may have a square, rectangular, or hexagonal cross-section, for example. However, the top surface is typically flat, i.e. in the X-Y plane of the reservoir.

(Each of) said raised strip(s) herein is typically substantial longitudinally extending, which means that its longitudinal extension is more than its transverse extension. This includes raised strip(s) that are completely longitudinally extending and straight; it includes raised strip(s) under an angle with the longitudinal axis of the reservoir, provided said angle is at the most 30'; this may include raised strip(s) that may be slightly curved (as described herein below); this includes raised strip(s) that may be wavy; this includes raised strip(s) that may comprise an angle(s), provided said angle is at least 120'; and provided that any such raised strip(s) extend more in longitudinal dimension than in transverse dimension, e.g. that any such raised strip(s) extend at least 50% or at least 100% more in longitudinal dimension than in transverse dimension.

In some embodiments, one or more of the raised strips (21) may be slightly curved, for example having a single curvature, as for example shown in the Figures, having a curvature with a radius that is at least equal to the average transverse dimension of the reservoir; and/or having a curvature following for example the contour of the closest longitudinal side edge. In some embodiments it may be preferred that the raised strips (21) are concave, wherein the longitudinal centre of the strip is closer to the longitudinal-axis of the reservoir (25) than the end point(s), and wherein the radius of curvature is at least 1 time, or optionally at least 1.5 times the average transverse dimension of the reservoir.

In some embodiments, the reservoir (25) is, in addition to said raised strip (21) or strips, composed of multitude of grooves, extending substantially in longitudinal dimension, or a multitude of rows of cavities, extending substantially in longitudinal dimension, for receiving the absorbent material (100) therein, with therein between said raised strip(s).

In some embodiments herein, said raised strips (21) have a contour, and adjacent either longitudinal side thereof, there is at least one such first row or groove, and adjacent thereto a second row and/or or groove, and said second row and/or groove may have a total volume less than the total volume of said first row or groove. Thereby, directly adjacent a channel (in the absorbent structure herein) the absorbent material (100) may have a higher basis weight than in a further adjacent zone.

In some embodiments herein, neighboring grooves or rows may be separated from one another but the spacing distance (in transverse dimension) between neighboring cavities (22) of neighboring rows or between neighboring grooves is less than 5 mm, and typically 4 mm or less, or 3.5 mm or less, or for example 3 mm or less.

Such grooves and/or rows may during the absorbent material (100) transfer mate with (coincide with) the portions of the substrate material that are between the neighboring rods (36), if present, and as described below, that extend substantially in longitudinal dimension; and hence, the areas between neighboring grooves and/or rows may mate (coincide) during absorbent material (100) transfer with the portions (strips) of the supporting sheet (200) that are on said rods (36), if present, as described below.

The cavities (22) may have any dimensions and shape, including cubical, rectangular, cylindrical, semi-spherical, conical, or any other shape. This may be any suitable number of cavities, but for example at least 20 or at least 50.

The cavities (22) may be present as identical cavities (22) or they may vary in dimension(s) or shape. The exact pattern, dimensions etc. will depend on the required structure to be formed, but may for example also depend on the particle size of the absorbent material, process speed etc.

In some embodiments at least 30% of the surface area of the reservoir (25) of the first moving endless surface (20) comprises said cavities, optionally at least 40%; and optionally up to 60% or up to 55%.

The distance in longitudinal dimension between the centre point of a cavity (22) (said centre point being in the plane of the outer surface of the first moving endless surface) and the centre point of a neighboring cavity (22) (in a row of cavities (22)) may for example be at least 3 mm, or at least 4 mm, or at least 6 mm, or for example up to 40 mm or up to 30 mm or up to 20 mm. This may apply to all such distances between neighboring cavities (22) in longitudinal dimension, or this may be an average over all such distances.

The distance in transverse dimension between the centre point of a cavity (22) or groove (said centre point being in the plane of the outer surface of the first moving endless surface) and the centre point of a neighboring cavity (22) or groove (in a transverse line of cavities) may for example also be as above. In some embodiments, the shortest distance in transverse dimension between two neighboring cavities (22) of a line of cavities (22) or between neighboring grooves is 4.0 mm or less.

In some embodiments, the longitudinal dimension of a cavity (22) may be (on average over all cavities (22) and/or for each cavity; measured over the outer surface of the first moving endless surface) at least 1 mm, or at least 2 mm, or at least 4 mm, and for example at the most 20 mm or at the most 15 mm. The transverse dimension may be within the same ranges as above, or it may even be the same as the longitudinal dimensions for one or more or each cavity.

Said rows or grooves may extend substantially parallel to, and equally spaced from, one another and/or said lines may extend substantially parallel to, and equally spaced from, one another.

In some embodiments, two or more of the rows or grooves, or part thereof, may be in the form of the longitudinal side edges of the raised strip, to which they are adjacent (and hence typically parallel), e.g. having the same curvature, angle etc as described herein.

The reservoir, cavities (22) or grooves may have any suitable dept dimension, and it may depend for example on the height of the first moving endless surface (20) (e.g. radius), the thickness of the desired structure to be produced, the particle size of the material, etc. The maximum depth of a reservoir, cavities (22) or grooves and/or the average maximum depth (average over all maximum depths of all cavities (22) and/or grooves) may for example be at least 1 mm, or at least 1.5 mm, or for example 2 mm or more, and for example up to 20 mm, or up to 15 mm, or in some embodiment herein, up to 10 mm, or to 5 mm, or to 4 mm.

According to some embodiments herein, the cavities (22) may have a an average dimension in longitudinal dimension and in transverse dimension of from 2 to 8 mm or from 3 mm to 7 mm; and the cavities (22) may have a maximum depth and/or average maximum depth of for example from 1.5 mm to 4 mm.

A scraper or doctor blade may be used to remove excess absorbent material. Excess material may be removed from the reservoir (25) and recycled back to e.g. the hopper One possibility to hold the material in the reservoir (25) (or its grooves or cavities) may be a vacuum applied to the inner side of the first moving endless surface, e.g. print roll or drum, in combination with suction apertures in (the bottom) of the reservoir, or of the grooves, or of cavities (22) thereof, to thus apply the vacuum suction onto the absorbent material. The vacuum is for example released just before or at the meeting point. The vacuum may be any vacuum pressure such as for example at least 10 kPa, or at least 20 kPa.

The vacuum may be provided by providing one or a plurality of vacuum chambers (28) in said first moving endless surface (20) (e.g. in its interior), wherein said vacuum can be applied, reduced, increased, and released (disconnected), depending on the position thereof in the process/apparatus.

Additional air pressure may be applied to said absorbent material (100) close to or at the meeting point, by provision of an air chamber (29) to ensure that the material flows to the supporting sheet (200) on said second moving endless surface.

Second Moving Endless Surface (30)

The method and apparatus (1) herein deploy a second moving endless surface (30), moving, like the first moving endless surface, in a machine direction (MD). It has an outer shell with one or more forming receptacle (s) (33), for receiving thereon or therein the supporting sheet (200) (which may be a web material, as described herein below, or individual sheets that are placed on a receptacle (33)). The following is described for a single receptacle (33) but may apply to each receptacles (33) of the second moving endless surface's outer shell.

Each receptacle (33) corresponds typically to an absorbent structure to be produced, as suitable for an absorbent article. The supporting sheet (200) may be a web material, so the method and apparatus (1) herein can thus serve to produce a web of such absorbent structures that are then subsequently separated into individual structures.

The second moving endless surface (30) may have or be a rotating surface, such as a rotating, e.g. cylindrical, drum. It may be that the outer shell moves, e.g. rotates, around a stationary inner chamber, e.g. a so-called stator.

The outer shell and the receptacle (33) have an average transverse dimension, which may for example be the cross-machine (CD) dimension, and the receptacle (33) has an average longitudinal dimension perpendicular thereto, which may for example be the machine dimension.

The receptacle (33) is at least partially air-permeable. It typically has an area that serves to receive said absorbent material, and this area is substantially in air-communication with a vacuum system, i.e. air permeable.

The receptacle (33) has one or more, optionally at least 2, substantially mating strips (31), that substantially mate (coincide) with said raised portion (but without contacting these directly), herein referred to as mating strips (31). Said mating strip(s) may not be in air communication with said vacuum system, i.e. it may be air impermeable. They may have thereto e a surface in the plane of the receptacle (33) that has no apertures.

A receptacle (33) has typically the same number of mating strips (31) as the number of raised strips (21) of a reservoir (25) of the first moving endless surface.

A raised strip (21) coincides (and hence mates with) a mating strip (31) during the transfer of the absorbent material (100) herein, i.e. during absorbent material (100) transfer to said second moving endless surface, said raised strip (21) substantially overlaps said mating strip. This typically applies to each mating raised strip (21) and mating strip. In other words, each raised strip (21) typically has a corresponding mating strip. It should be understood that the raised strip (21) and mating strip (31) do not directly touch during the absorbent material (100) transfer (the supporting sheet (200) material is in between them). The supporting sheet (200) may or may not touch the raised strip(s) (21); typically it does not.

The receptacle (33) has peripheral edges, and peripheral edge zones, including opposing longitudinal edges and edge zones, and a transverse front edge and front edge zone, and a transverse back edge and back edge zone. Each of said front and back edge zones, extending the complete transverse dimension, may for example have a longitudinal dimension of from about 5% to about 20%, or to 15%, or to 10% of the average longitudinal dimension of the receptacle (33). Each of said longitudinal edge zone may extend the length and may have an average transverse dimension of for example from about 5% to about 20%, or typically to about 15% or to about 10% of the average transverse dimension of the receptacle (33). In some embodiments, the mating strips (31) is not present in any of the edge zones.

The receptacle (33) may in addition, or alternatively, comprise a front region, back region and central region, therein between, as further described below. The central region may be for example the central ⅓ of the receptacle (33), extending the full transverse dimension. In some embodiment, the mating strip(s) are present only in the front region; alternatively, in some embodiments, the mating strip(s) are present in the central region only or at least; alternatively, in some embodiments, the mating strip(s) are present in the central region and front region and optionally in the back region. It may alternatively or in addition be preferred that one or more mating strips (31) are present in the central region and front region. To provide improved liquid transportation and more efficient absorbency by the whole absorbent structure, it may be preferred to have said mating strip(s) at least in the central region and optionally extending also at least in the front region.

In any such case, it may be preferred that none of the edge zones described above comprises such mating strips (31).

The following is described for a mating strip, in relation to its corresponding raised strip, but may be, and optionally is, applicable to each mating strip (31) (and its corresponding raised strip).

A mating strip (31) and the corresponding raised strip (21) may have the same size and shaped and surface area, and be hence completely mating. It may be that a raised strip (21) has a surface area that is slightly more than the surface area of a corresponding mating strip. Hereby, the mating strip (31) and the corresponding raised strip (21) then typically still have substantially the same overall shape.

In some embodiments, it may be preferred that at least the average length of a mating strip (31) and the average length of a corresponding mating step are substantially the same, the difference for example being at the most 20%, or for example the raised strip (21) having an average length that is at the most 10% more than the average length of the corresponding mating strip. The average length L' of a mating strip (31) is hence from about 0.8×L to 1.2×L, or for example from 0.9×L to 1.1×L, or to 1×L, (L being the average length or the corresponding raised strip).

In some embodiments, it may be preferred (in addition or as alternative of the above) that a mating strip (31) may have an average width W' that is less than the average width W of the raised strip, but in some embodiments, W' is not more than W. Hence, W' is from 0.5×W to 1.2×W, or for example from 0.66×W, or for example from 0.8×W, to for example 1×W, or for example to 0.9×W.

W' may for example be at least 2.5 mm, or for example at least 4 mm or for example at least 6 mm. W' may be less 20 mm or less, or less 15 mm or less, or for example 10 mm or less.

Thus in some embodiments, a raised strip (21) is completely overlapping a corresponding mating strip (31) during the absorbent material (100) transfer, but a mating strip (31) is not substantially overlapping a corresponding raised strip. This may help spreading of the deposited absorbent material (100) slightly on said supporting sheet (200), to ensure a more homogeneous deposition thereof on said supporting sheet (200).

Each mating strip (31) extends typically at the most 90% of the longitudinal dimension of the receptacle (33), or for example at the most 80% or at the most 70%.

Thus, the average length of a mating strip (31) may be 90% or less of the average length of the receptacle (33), or for example at the most 80% or at the most 70%.

The receptacle (33) may have for example at least two mating strips (31) on either side of the longitudinal axis of the receptacle (33), and being mirror images of one another. They may be straight or for example curved, with a radius of curvature as describe herein.

The receptacle (33) may also for example have 3 or 4, or for example 5 or for example 6 mating strips (31). Two or more thereof may be parallel to one another.

The receptacle (33) may have for example 3, or 4, or 5, or 6 mating strips (31) that are at least present in the central region, and optionally extend in the front region and optionally in the back region; they may be parallel to one another and/or they may be such that those on one longitudinal side of the longitudinal axis of the receptacle (33) are mirror images of those that are on the opposite longitudinal side.

The receptacle (33) may have for example two mating strips (31) in the front region, on either side of the longitudinal axis, and mirror images of one another therein; and two mating strips (31), extending in at least the central region, on either side of the longitudinal axis, and mirror images of one another therein; and optionally two mating strips (31) in the back region, on either side of the longitudinal axis, and mirror images of one another therein.

In some embodiments, there may be no mating strip (31) coinciding with the longitudinal axis of the receptacle (33), but only on either side thereof. This may help to ensure an absorbent structure formation into a U-shape during sue, rather than a V-shape, which may be better for fit and/or absorbency.

In some embodiments, at least two mating strips (31) extend, and hence have an average length (longitudinal dimension) of are at least 50% of the average length of said receptacle (33).

In some embodiments, there are at least an additional two mating strips (31) that have an average length that is less than 50% of the average length of the receptacle (33).

The mating strip (31) cross-section in the X-Z plane may be any form. It may have a square, rectangular, or hexagonal cross-section, for example. However, the tops surface that supports the supporting sheet (200) is typically flat, i.e. in the X-Y plane of the receptacle (33).

(Each of) said mating strip(s) (31) herein is typically substantial longitudinal extending, which means that its longitudinal extension is more than its transverse extension. This includes mating strip(s) (31) that are completely longitudinally extending and straight; it includes mating strip(s) under an angle with the longitudinal axis of the reservoir, provided said angle is at the most 30°; this may include mating strip(s) that may be slightly curved (as described herein below); this includes mating strip(s) that may be wavy; this includes mating strip(s) that may comprise an angle(s), provided said angle is at least 120°; and provided that any such mating strip(s) extend more in longitudinal dimension than in transverse dimension, e.g. that any such mating strip(s) extend at least 50% or at least 100% more in longitudinal dimension than in transverse dimension.

In some embodiments, one or more of the mating strips (31) may be slightly curved, for example having a single curvature, having a curvature with a radius that is at least equal to the average transverse dimension of the reservoir; and/or having a curvature following for example the contour of the closest longitudinal side edge. In some embodiments it may be preferred that the mating strips (31) are concave, wherein the longitudinal centre of the strip is closer to the longitudinal-axis of the reservoir (25) than the end point(s), and wherein the radius of curvature is at least 1 time, or optionally at least 1.5 times the average transverse dimension of the reservoir.

The receptacle (33) area other than said mating strips (31) may for example be a mesh material that hence has apertures and is in air communication with said vacuum system (38), e.g. being air permeable.

The surface area of the receptacle (33), other than the mating strips (31), may alternatively comprise thin supports substantially in transverse, for supporting the supporting sheet (200), as for example shown in FIG. 3, i.e. typically having a maximum dimension in longitudinal direction which may be less than the average width dimension of the adjacent mating strip; and/or for example at the most 4 mm, or for example at the most 3 mm.

As for example shown in FIG. 4, the receptacle (33) may further comprise a multitude of substantially longitudinally extending rods (36), spaced apart from one another, and typically from a neighboring mating strip, in transverse direction. Such rods (36) may then partially form the most outer surface of said receptacle (33), so that the supporting sheet (200) is received and carried by said rods (36) and said mating strips (31).

Between rods (36), or between rods (36) and a neighboring mating strip, there is then a spacing where the supporting sheet (200) may not be supported directly by the receptacle (33)'s mating strips (31) or rods (36).

The receptacle (33) may comprise said rods (36) over substantially the whole length (longitudinal dimension) of the receptacle (33); or for example over the whole length except the front edge zone and/or back edge zone; or, in some embodiments herein, the rods (36) may be present only in said central region; in some embodiments, the rods (36) may be present in the front region and optionally the central region, but not the back region; in some embodiments, the rods (36) may be present in the back region and optionally the central region, but not the front region.

The receptacle (33) may comprise such rods (36) over the whole width (longitudinal-dimension) of said receptacle (33); or for example over the whole width except in said longitudinal edge zones.

In any of these embodiments, the zone(s) or region(s) not comprising said rods (36) is herein referred to as rod-free zone or rod-free region; in said rod-free region or rod-free zone the supporting sheet (200) is then deposited onto said mating strips (31) and optionally said inner grid (e.g. a mesh material) directly.

Said receptacle (33) may have in said region(s) or zone(s) that not comprising said rods (36) a higher friction than said rods (36). This can aid to ensure the supporting sheet (200) is pulled in between the rods (36), or rods (36) and mating strips (31), in the low friction zone, and less or not at all in the high friction zone. For example, the receptacle (33) can be made of a higher friction material (e.g. a material with a less even surface), or may be treated with an friction-increasing agents, in those zones or regions not comprising said rods (36); or for example said zones or regions with rods (36), or only said rods (36), can be made of a lower friction material, or treated with friction-reducing agent.

A rod (36), if present, is substantial longitudinally-extending, which means for the purpose of the invention the same as defined above for the mating strip.

The rod (36) may be any shape or form. It may have a square, rectangular, round, oval or hexagonal cross-section in CD, for example. Each rod has a top portion (which may be the top surface for, for example, rods (36) that have a square or rectangular cross-section) and an opposing bottom portion or surface. Said top portion or surface is then in contact with the supporting sheet (200); said bottom surface may be adjacent (e.g.: on) an, at least partially, air-permeable inner grid.

In some embodiments, it may be preferred that the rod is generally rectangular with optionally a triangular-shaped top portion.

The minimum distance between neighboring rods (36) or neighboring rods (36) and a mating strip (31) is for example (in transverse dimension) at least 2 mm, or at least 3 mm, or at least 5 mm, or for example at least 10 mm.

Two or more rods (36) may be parallel to one another, so that the spacing distance between parallel neighboring rods (36), in transverse dimension, is at least said 2 mm along substantially the whole length.

Thus, there may be a void volume between neighboring rods (36), or between a rod and a neighboring mating strip, and said void volume extends substantially in machine direction. This void volume can serve to receive the supporting sheet (200) therein, as an undulation, and then optionally said absorbent material (100) therein.

Each rod may have a maximum cross-machine dimension which may be at least 0.1 mm, optionally at least 0.3 mm, or at least 0.5 mm, and for example less than 4 mm, or less than 2 mm.

The receptacle (33) may for example have at least 2 such rods (36), or for example at least 4 such rods (36), or for example at least 5 or at least 7 such rods (36).

Said rods (36) may be straight in longitudinal direction and/or they may for example be parallel to a neighboring mating strip.

In some preferred embodiments, the supporting sheet (200) is deposited onto said mating strips (31) and optional rods (36) and it bends in between neighboring mating strips (31) and/or rods (36), e.g. due to the vacuum suction, to form thereby in said sheet undulations between neighboring rods (36) and/or mating strips (31), and crests supported on said rods (36)/mating strips (31) (on said top surface or top portion). (The inner grid may control/determine the size (height) of said undulations.)

The supporting sheet (200) is transferred from a transfer means, such a transfer roll (210), to said second moving endless surface (30) and deposited onto said outershell/receptacle(s) (33). It may be transported to the outershell and receptacle (33) thereof as a web, or as individual sheets. The supporting sheet (200) may be a nonwoven material, as further described herein.

Subsequently, said absorbent material (100) may be deposited onto said supporting sheet (200), on said receptacle (33), such that substantially no material is deposited on the portions of the supporting sheet (200) that are on the mating strips (31).

The absorbent material (100) may be deposited such that it is only present on the portions of the supporting sheet (200) (e.g. strips of supporting sheet (200)) that is present between neighboring rods (36) and/or mating strips (31), e.g. in said undulations. Thereto, specific first moving surface may be used that has the specific grooves or cavities (22) that mate with said undulations, and not with said rods (36) as described below may be used.

Alternatively, or in addition, the vacuum may be such that it pulls the absorbent material (100) to or towards the portions of the supporting sheet (200) present between neighboring rods (36) and/or mating strips (31), e.g. into said undulations. Substantially no absorbent material (100) may for example be present on the supporting sheet (200) present on said rods (36), (not on said mating strips (31), as set out herein above already), e.g. on said crests of said supporting sheet (200).

Alternatively, or in addition, absorbent material (100) deposited onto the portions of the supporting sheet (200) on said rods (36) (e.g. said crests) may be removed by means known in the art, such as a scraper or doctor blade.

Alternatively, or in addition, the supporting sheet (200) may comprise adhesive. For example said adhesive may be present on said portions of said supporting sheet (200) that are between neighboring rod and/or mating strips (31), e.g. said undulations. This may help to adhere the absorbent material (100) in such portions, e.g. on said undulations. The supporting sheet (200) may then, prior to addition of the absorbent material, comprise no adhesive applied on said portions supported by said rods (36) and/or mating strips (31), e.g. said crests, so that less or no absorbent material (100) adheres in said portions, e.g. crests.

In some embodiments, the second moving endless surface (30) may for example have a speed of at least 1000 part per minute and/or a speed of at least 4.5 m/s, or at least 6 m/s, or at least 8 m/s.

Absorbent Material (100)

The absorbent material (100) herein is optionally a flowable material (in the dry state), such as a particulate material; it may be any material in particulate form, which includes particles, flakes, fibers, spheres, agglomerated particles and other forms known in the art.

The absorbent material (100) comprises superabsorbent polymer material (e.g. particles), optionally combined with cellulosic material (including for example cellulose, comminuted wood pulp in the form of fibers). In some embodiment, the absorbent material (100) may comprise at least 60%, or at least 70% by weight of superabsorbent polymer material, and at the most 40% or at the most 30% of cellulosic material. In some other embodiments, the absorbent layer comprises absorbent material (100) that consists substantially of absorbent polymer material, e.g. particles, e.g. less than 5% by weight (of the absorbent material) of cellulosic material is present; and said absorbent layer/absorbent structure, may be free of cellulosic material.

In some embodiments herein, the absorbent material, e.g. the particulate absorbent material, comprises at least, or consists essentially of or consists of, (particulate) superabsorbent polymer material, herein referred to as SAP, and also known as particulate absorbent gelling material, AGM. The particulate SAP herein may have a high sorption capacity, e.g. having a CRC of for example at least 20 g/g, or at 30 g/g. Upper limits may for example be up to 150 g/g, or up to 100 g/g.

The particulate SAP may have a good permeability for liquid, for example, having a SFC value of at least $10\times10^{-7}$ cm$^3$ s/g; or optionally at least $30\times10^{-7}$ cm$^3$.s/g, or at least $50\times10^{-7}$ cm$^3$ s/g $10\times10^{-7}$ cm$^3$ s/g, or possibly permeability SFC value of at least $100\times10^{-7}$ cm$^3$ s/g, or at least a SFC of $120\times10^{-7}$ cm$^3$ sec/g. This SFC is a measure of permeability and an indication of porosity is provided by the saline flow conductivity of the gel bed as described in U.S. Pat. No. 5,562,646, (Goldman et al.) issued Oct. 8, 1996 (wherein however a 0.9% NaCl solution is used instead of Jayco solution). Upper limits may for example be up to 350 or up to $250(\times10^{-7}$ cm$^3$.s/g).

In some embodiments herein the polymers of said SAP are internally cross-linked and/or surface crosslinked polymers.

In some embodiments herein, the absorbent material (100) comprising or consisting of particles of polyacrylic acids/polyacrylate polymers, for example having a neutralization degree of from 60% to 90%, or about 75%, having for example sodium counter ions, as known in the art; they may be surface crosslinked and/or internally crosslinked polyacrylic acid/polyacrylate polymers.

In some embodiments herein, the absorbent material (100) is in the form of particles with, a mass medium particle size up to 2 mm, or between 50 microns and 2 mm or to 1 mm, or optionally from 100 or 200 or 300 or 400 or 500 µm, or to 1000 or to 800 or to 700 µm; as can for example be measured by the method set out in for example EP-A-0691133. In some embodiments of the invention, the material is in the form of particles whereof at least 80% by weight are particles of a size between 50 µm and 1200 µm and having a mass median particle size between any of the range combinations above. In addition, or in another embodiment of the invention, said particles are essentially spherical. In yet another or additional embodiment of the invention the absorbent material (100) has a relatively narrow range of particle sizes, e.g. with the majority (e.g. at least 80% or optionally at least 90% or even at least 95% by weight) of particles having a particle size between 50 µm and 1000 µm, optionally between 100 µm and 800 µm, and more optionally between 200 µm and 600 µm.

The absorbent material (100) herein may advantageously comprise less than 15% by weight of water, or less than 10%, or less than 8% or less than 5%. The water-content can be determined by the Edana test, number ERT 430.1-99 (February 1999) which involves drying the particulate material (100) at 105° Celsius for 3 hours and determining the moisture content by the weight loss of the particulate material (100) after drying.

The particulate SAP herein may be particles of SAP that are surface coated or surface treated (this not including surface-crosslinking, which may be an additional surface-treatment); such coatings and surface treatment steps are well known in the art, and include surface treatment with one or more inorganic powders, including silicates, phosphates, and coatings of polymeric material, including elastomeric polymeric materials, or film-forming polymeric materials.

Supporting Sheet (200)

The absorbent structure producible with the apparatus (1) and method of the invention comprises a supporting sheet (200), to receive the absorbent material. This supporting sheet (200) may be any individual sheet or web sheet material, in particular paper, films, wovens or nonwovens, or laminate of any of these.

In some embodiments herein, the supporting sheet (200) is a nonwoven, e.g. a nonwoven web, such as a carded nonwoven, spunbond nonwoven or meltblown nonwoven, and including nonwoven laminates of any of these.

The fibers may be of natural or man-made origin and may be staple or continuous filaments or be formed in situ. Commercially available fibers have diameters ranging typically from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheet-core arrangement, e.g. with different polymers forming the sheet and the core. Nonwoven fabrics can be formed by many processes such as meltblowing, spunbonding, solvent spinning, electrospinning, and carding. The basis weight of nonwoven fabrics is usually expressed in grams per square meter (gsm).

The nonwoven herein may be made of hydrophilic fibers; "Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The supporting sheet (200) herein may be air-permeable. Films useful herein may therefore comprise micro pores. Nonwovens herein may for example be air permeable. The supporting sheet (200) may have for example an air-permeability of from 40 or from 50, to 300 or to 200 $m^3/(m^2 \times min)$, as determined by EDANA method 140-1-99 (125 Pa, 38.3 $cm^2$). The supporting sheet (200) may alternatively have a lower air-permeability, e.g. being non-air-permeable, to for example be better detained on a moving surface comprising vacuum.

In preferred executions, the supporting sheet (200) is a nonwoven laminate material, a nonwoven laminate web, for example of the SMS or SMMS type.

In order to form easily said undulations, the supporting sheet (200) may have a basis weight that is less than 60 gsm, or for example than 50 gsm, for example from 5 gsm to 40 gsm, or to 30 gsm.

The supporting sheet (200) may have a transverse-extensibility or a longitudinal-extensibility, for example of more the 20%, or for example more than 100%, but for example not more than 200%.

In one of the embodiment herein, the supporting sheet (200) has a transverse dimension that is more than the transverse dimension of the part of the receptacle (33), e.g. at least 10%, or for example at 20% or at least 30%, and for example up to about 120%.

Adhesive Application Units (50; 51) and Method Steps.

The supporting sheet (200) may comprise and adhesive prior to transfer to said second moving endless surface. Thus, the apparatus (1) herein may comprise a (second) adhesive application unit (51) upstream from said second moving endless surface, and for example downstream from said supporting material transfer means, e.g. roll. The method herein may thus comprise such an adhesive application step.

This adhesive may be applied uniformly and/or continuously, to aid absorbent material (100) immobilization and then it may help to adhere the supporting sheet (200) to a further material that may overlay the absorbent layer, as described below. Alternatively, it may be applied in a pattern. It may be applied by spraying, or for example by selectively slot-coating; the apparatus (1) may thus comprise a slot-coater, with a pattern.

The adhesive may be applied on those portions of the supporting sheet (200) that are to receive to receive the absorbent material; then, it helps to immobilize the absorbent material (100) thereon (e.g. to ensure the absorbent material (100) will stay substantially as applied, with said channels, optionally not only during manufacturing, but also during storage and in use (at least during part of the use). Or, alternatively, only on those portions of the supporting sheet (200) that are to be on said mating strips (31); then it may help to adhere the supporting sheet (200) to a further material that may overlay the absorbent layer, as described below. It may be applied as substantially longitudinal stripes, for example.

In some embodiments, the apparatus (1) may comprise a unit to apply an adhesive to said supporting sheet (200) in a pattern, for example the pattern of the mating strips (31), and optionally of the rods (36), if present.

Any suitable adhesive can be used for this, for example so-called hotmelt adhesives used. For example, a sprayable hot melt adhesives, such as H.B. Fuller Co. (St. Paul, Minn.) Product No. HL-1620-B, can be used.

Alternatively, or in addition, it may be beneficial to apply a further immobilization adhesive to said absorbent structure produced by the apparatus (1) or method herein, e.g. to ensure the absorbent material (100) will stay substantially as applied, with said channels, optionally not only during manufacturing, but also during storage and in use (at least during part of the use). This immobilization adhesive may then for example be applied onto said absorbent layer just after application of said absorbent material (100) onto said supporting sheet (200).

The apparatus (1) herein may thus have a further (first) adhesive application unit (50), e.g. downstream from said second moving endless surface meeting point. The method may have a corresponding method step This adhesive may be applied uniformly and/or homogeneously. This may be a thermoplastic adhesive material.

In accordance with certain embodiments, the thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or −6° C.>Tg<16° C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins. In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%. In certain embodiments, the thermoplastic adhesive material is present in the form of fibers. In some embodiments, the fibers will have an average thickness of about 1 to about 50 micrometers or about 1 to about 35 micrometers and an average length of about 5 mm to about 50 mm or about 5 mm to about 30 mm.

Further Method Steps/Apparatus Units

The apparatus (1) and method herein may comprise the further step/unit, of applying a further supporting sheet (300) onto said absorbent structure, to enclose said absorbent material, as know in the art. This may be done such that a channel or each channel of a first absorbent structure corresponds with a channel of the second absorbent structure.

The apparatus (1) and method herein may alternatively or in addition comprise the apparatus (1) unit/method step of folding the supporting sheet (200) over the absorbent material (100) to enclose it thereby. It may comprise a sealing unit, sealing step to seal the two supporting sheet (200) or the folded supporting sheet (200) along the peripheral edges of the absorbent layer.

The absorbent structure may alternatively or in addition be combined with other layers, such as an acquisition layer, or topsheet and the apparatus (1) and method herein may comprise according steps/units.

The method or apparatus (1) herein may be to produce an absorbent core or structure that comprises two or more of the above described absorbent structures; for example two such layers, superposed on one another such that the absorbent material (100) of a first layer and the absorbent material (100) of the other second layer are adjacent one another and sandwiched between the supporting sheet (200) of the first layer and the supporting sheet (200; 300) of the second layer. The apparatus (1) herein may thus be a combination apparatus, comprising two or more, e.g. two, of the apparatuses described herein, to produce two or more, e.g. two, absorbent structures, and then comprising a combining unit to combine the absorbent structures. The method may comprise according method step(s).

The absorbent structure produced with the method/apparatus (1) of the invention herein may also be combined with an absorbent structure produced by a method/apparatus (1) other than of the present disclosure, said combination may be done as set out above.

The apparatus (1) may comprise a pressure means (70), such as a pressure roll, that can apply pressure onto the absorbent structure, and typically an absorbent structure wherein the absorbent material (100) is sandwiched between the supporting sheet (200) and a further material; the pressure may be applied onto said supporting sheet (200) or on any of the further material/layer that placed over the absorbent layer, as described above in this section. The method herein may then comprise a corresponding method step.

This pressure application may optionally be done to selectively apply pressure only onto the channels of the absorbent structure, e.g. on the portions of the supporting sheet (200) that correspond to the channels, and that thus not comprise (on the opposed surface) absorbent material, to avoid compaction of said absorbent material (100) itself.

Thus, the apparatus (1) may comprise a pressure means (70) that has a raised pressuring pattern (71) corresponding to said pattern of the raised strip(s) and/or of said mating strip(s), in some optionally corresponding to the pattern of the mating strip(s). The method may have an according method step.

Absorbent Articles

The apparatus (1) and method of the invention are for example useful to produce absorbent structures, or absorbent cores (i.e. said structures combined with a further material, described herein) suitable for absorbent articles.

Absorbent articles may include diapers, including fastenable diapers and (refastenable) training pants; adult incontinence undergarments (pads, diapers) feminine hygiene products (sanitary napkins, panty-liners), breast pads, care mats, bibs, wound dressing products, and the like. Ins some preferred embodiments, the absorbent article is a diaper, or adult incontinent product.

The absorbent article herein may comprise in addition to the absorbent structure or absorbent core, a topsheet and backsheet, and for example one or more side flaps or cuffs. The topsheet or cuffs or side flaps may comprise a skin care composition or lotion or powder, known in the art, panels, including those described in U.S. Pat. No. 5,607,760; 5,609, 587; 5,635,191; 5,643,588.

Preferred absorbent articles herein comprise a topsheet, facing the wearer in use, for example a nonwoven sheet, and/or an apertured sheet, including apertured formed films, as known in the art, and a backsheet.

The backsheet may be liquid impervious, as known in the art. In preferred embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind. and sold under the trade names X15306, X10962 and X10964.

The backsheet, or any portion thereof, may be elastically extendable in one or more directions. The backsheet may be attached or joined to a topsheet, the absorbent structure or core described herein, or any other element of the diaper by any attachment means known in the art.

Diapers herein may comprise leg cuffs and/or barrier cuffs; the article then typically has a pair of opposing side flaps and/or leg and/or barrier cuffs, each of a pair being positioned adjacent one longitudinal side of the absorbent structure or core, and extending longitudinally along said structure or core, and typically being mirror images of one another in the longitudinal-axis of the article; if leg cuffs and barrier cuffs are present, then each leg cuffs is typically positioned outwardly from a barrier cuff. The cuffs may be extending longitudinally along at least 70% of the length of the article. The cuff(s) may have a free longitudinal edge that can be positioned out of the X-Y plane (longitudinal/transverse directions) of the article, i.e. in z-direction. The side flaps or cuffs of a pair may be mirror images of one another in the Y-axis (longitudinal axis) of the article. The cuffs may comprise elastic material.

The diapers herein may comprise a waistband, or for example a front waistband and back waist band, which may comprise elastic material.

The diaper may comprise side panels, or so-called ear panels. The diaper may comprise fastening means, to fasten the front and back, e.g. the front and back waistband. Preferred fastening systems comprise fastening tabs and landing zones, wherein the fastening tabs are attached or joined to the back region of the diaper and the landing zones are part of the front region of the diaper.

The absorbent article may also include a sub-layer disposed between the topsheet and the absorbent structure or core, capable of accepting, and distributing and/or immobilizing bodily exudates. Suitable sublayers include acquisition layers, surge layers and or fecal material storage layers, as known in the art. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, optionally looped, strands of fibers, or optionally apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for making an absorbent structure for an absorbent article, the absorbent structure comprising a supporting sheet and thereon an absorbent layer with a longitudinal dimensional and transverse dimension and a height dimension, the absorbent layer comprising an absorbent material with therein one or more channels that are substantially free of absorbent material, the apparatus comprising:

a first moving endless surface having an absorbent layer-forming reservoir with a longitudinal dimension and averaged length, a perpendicular transverse dimension and average width, and, perpendicular to both, a depth dimension and average depth, and a void volume for receiving absorbent material therein, the reservoir comprising a substantially longitudinally extending raised strip having an average width W of at least 5% of the average width of the reservoir, and an average length L of at least 5% and at the most 80% of the average longitudinal dimension of the reservoir;

a feeder for feeding absorbent material to the first moving endless surface;

a second moving endless surface having an outer shell including an air permeable receptacle for receiving a supporting sheet the receptacle having a substantially longitudinally extending mating strip having an average width W' being from 0.5×W to 1.2×W, and having an average length L'being from 0.8×L to 1.2×L;

a vacuum system connected to the outer shell, the vacuum system adapted to facilitate retention of the supporting sheet and the absorbent material on the outer shell; and wherein, in a meeting point, the first moving endless surface and the second moving endless surface are adjacent and in close proximity of one another during transfer of absorbent material from the first moving endless surface to the second moving endless surface; and wherein the mating strip is arranged to mate with the raised strip during transfer of the absorbent material.

2. The apparatus of claim 1, wherein W is at least 5 mm and L is at least 30 mm, and W' is at least 2.5 mm.

3. The apparatus of claim 1, wherein the reservoir is formed by a multitude of cavities with a void volume, for receiving the absorbent material therein, and W being at least 6 mm.

4. The apparatus of claim 3, wherein the cavities have each a maximum dimension in a transverse direction which is at least 3 mm, and wherein a shortest distance between directly neighboring cavities in the transverse direction is less than 5 mm.

5. The apparatus of claim 1, wherein the reservoir, excluding the raised strips, has apertures to be partially air permeable and wherein the first moving endless surface has a cylindrical surface with the reservoir rotatably moving around a stator comprising a vacuum chamber connected to the vacuum system; and wherein the second outershell is cylindrical rotatably moving around a stator comprising a vacuum chamber connected to the vacuum system.

6. The apparatus of claim 1, wherein the raised strip defines a total surface area (in a plane of the first moving endless surface) is from 3% to 20% of a total surface area (in the plane of the first moving endless surface) of the reservoir.

7. The apparatus of claim 1, comprising:

at least two mating strips, the at least two mating strips are mirror images of one another with respect to a longitudinal axis of the receptacle; and at least two raised strips being mirror images of one another with respect to a longitudinal axis of the reservoir.

8. The apparatus of claim 1, wherein the receptacle further comprises a multitude of substantially longitudinally extending rods spaced apart from one another in transverse direction, each rod having a maximum width dimension of at least 0.3 mm and less than 2.5 mm, the rods each having an average height dimension of at least 1 mm, and wherein top surfaces of the rods and the mating strips in the same plane of the receptacle.

9. The apparatus of claim 1, wherein the reservoir is formed by a multitude of cavities, and wherein cavities that are directly adjacent the raised strip have volumes that are greater than volumes of cavities that are not directly adjacent the raised strip.

10. The apparatus of claim 1, comprising an adhesive application unit positioned upstream from the meeting point.

11. The apparatus of claim 1, comprising downstream from the meeting point a unit to cover the absorbent layer with a further material, selected from a unit for folding the supporting sheet over the absorbent layer; a unit for applying a further supporting sheet; a unit for applying a further layered material, for example an acquisition material; a unit for combining the structure with a further absorbent structure.

12. The apparatus of claim 1, comprising a downstream pressure roll with a raised pressure pattern substantially corresponding to the mating strip, for contacting the supporting sheet in an area thereof corresponding to a channel.

* * * * *